US009730594B2

(12) United States Patent
Komine et al.

(10) Patent No.: US 9,730,594 B2
(45) Date of Patent: Aug. 15, 2017

(54) ARTERIAL-WALL STIFFNESS EVALUATION SYSTEM

(75) Inventors: Hidehiko Komine, Ibaraki (JP); Yoshiyuki Asai, Ibaraki (JP); Takashi Yokoi, Ibaraki (JP); Yukiyoshi Saito, Tokyo (JP)

(73) Assignees: NATIONAL INSTITUTE OF ADVANCE INDUSTRIAL SCIENCE AND TECHNOLOGY, Tokyo (JP); SHISEI DATUM CO., LTD., Tokyo (JP)

( * ) Notice: Subject to any disclaimer, the term of this patent is extended or adjusted under 35 U.S.C. 154(b) by 0 days.

(21) Appl. No.: 13/063,518

(22) PCT Filed: Sep. 17, 2008

(86) PCT No.: PCT/JP2008/066786
§ 371 (c)(1),
(2), (4) Date: Mar. 11, 2011

(87) PCT Pub. No.: WO2010/032293
PCT Pub. Date: Mar. 25, 2010

(65) Prior Publication Data
US 2011/0172546 A1  Jul. 14, 2011

(51) Int. Cl.
*A61B 5/021*   (2006.01)
*A61B 5/02*    (2006.01)
(Continued)

(52) U.S. Cl.
CPC .......... *A61B 5/021* (2013.01); *A61B 5/02007* (2013.01); *A61B 5/02116* (2013.01); *A61B 5/7239* (2013.01); *A61B 5/107* (2013.01)

(58) Field of Classification Search
CPC ..... A61B 5/021; A61B 5/022; A61B 5/02007; A61B 5/02116
(Continued)

(56) References Cited

U.S. PATENT DOCUMENTS 4,564,020 A  *  1/1986  Link ............................ 600/490
5,152,297 A  *  10/1992  Meister et al. ............... 600/485
(Continued)

FOREIGN PATENT DOCUMENTS

CN        1442110 A        9/2003
JP        05-038331        2/1993
(Continued)

OTHER PUBLICATIONS

International Search Report mailed Oct. 14, 2008, International Patent Application No. PCT/JP2008/066786.

*Primary Examiner* — Patricia Mallari
*Assistant Examiner* — Michael Catina
(74) *Attorney, Agent, or Firm* — Casimir Jones, S.C.

(57) ABSTRACT

An arterial-wall stiffness evaluation system of the present invention includes: a cuff to be attached to a part of a living body; a pressure sensor for detecting pressure in the cuff; a cuff-pressure control section for controlling the pressure in the cuff to be increased or decreased up to a predetermined value, based on a value detected by the pressure sensor; and a data processing section for calculating, based on pulse waves detected by the pressure sensor, pulse-wave amplitudes of cuff-pressure pulse waves and blood-pressure pulse waves, and for evaluating arterial-wall stiffness based on the pulse-wave amplitudes. The arterial-wall stiffness is evaluated by a pressure-diameter characteristic curve, which represents a relationship between vascular diameter and transmural pressure applied to a vascular wall, or by estimation from shapes and amplitudes of the detected pulse waves. Alternatively, the evaluation is performed by estimating, from the detected pulse waves, a differential function obtainable by differentiating a pressure-diameter characteristic curve with respect to a transmural pressure, or by use of an arctan or a sigmoid function. This allows anybody (Continued)

to easily evaluate blood vessel stiffness anytime with high accuracy even at home without any special knowledge.

1 Claim, 12 Drawing Sheets

(51) Int. Cl.
    *A61B 5/00*     (2006.01)
    *A61B 5/107*     (2006.01)

(58) Field of Classification Search
    USPC .................................. 600/481, 485, 490, 494
    See application file for complete search history.

(56) References Cited

U.S. PATENT DOCUMENTS

| | | |
|---|---|---|
| 5,582,179 A | 12/1996 | Shimizu |
| 5,711,303 A | 1/1998 | Shimizu |
| 6,309,359 B1 | 10/2001 | Whitt et al. |
| 6,626,840 B2 * | 9/2003 | Drzewiecki et al. ......... 600/490 |
| 7,056,291 B2 | 6/2006 | Yokozeki |
| 8,465,435 B2 * | 6/2013 | Van Goudoever et al. .. 600/485 |
| 2003/0167014 A1 | 9/2003 | Ogura |
| 2004/0044288 A1 * | 3/2004 | Gorenberg et al. ........... 600/481 |
| 2004/0220481 A1 * | 11/2004 | Yokozeki et al. ............. 600/485 |
| 2005/0119578 A1 | 6/2005 | Kubo |
| 2008/0039731 A1 * | 2/2008 | McCombie et al. .......... 600/485 |

FOREIGN PATENT DOCUMENTS

| | | |
|---|---|---|
| JP | 05-038332 | 2/1993 |
| JP | 07-124129 | 5/1995 |
| JP | 2004-223046 | 8/2004 |
| JP | 2006-141849 | 6/2006 |
| JP | 2008-228934 | 10/2008 |

* cited by examiner

TRANSMURAL PRESSURE = INNER PRESSURE − EXTERNAL PRESSURE

VASCULAR PRESSURE-DIAMETER CHARACTERISTIC CURVE

SYSTEM CONFIGURATION

ARCTAN MOST FIT TO ESTIMATED VASCULAR
PRESSURE-DIAMETER CHARACTERISTIC CURVE

TRANSMURAL PRESSURE ACROSS VASCULAR WALL

SIGMOID FUNCTION MOST FIT TO ESTIMATED VASCULAR
PRESSURE-DIAMETER CHARACTERISTIC CURVE

TRANSMURAL PRESSURE ACROSS VASCULAR WALL

IMAGE OF PRACTICAL USE

ARTERIAL-WALL STIFFNESS EVALUATION SYSTEM

CROSS REFERENCE TO RELATED APPLICATIONS

The present application is a Section 371 U.S. national stage entry of pending International Patent Application No. PCT/JP2008/066786, International Filing Date Sep. 17, 2008, which published on Mar. 25, 2010 as Publication No. WO 2010/032293, the contents of which are incorporated by reference in its entirety.

TECHNICAL FIELD

The present invention relates to an arterial-wall stiffness evaluation system in which how hard an arterial wall is can be easily evaluated even at home without using any large apparatus or complicated system installed in hospitals and the like.

BACKGROUND ART

Conventionally, there have been used various techniques for evaluating stiffness of vascular walls, such as a technique in which a beating state of blood vessels is measured with the use of a diagnostic imaging ultrasonic apparatus, a technique in which pulse-wave transmission velocity is measured, and a technique in which interference between traveling wave and reflected wave of a pulse wave that travels through a blood vessel is measured. The measurements by these techniques need large apparatuses, and therefore should be conducted as a checkup in specialized facilities such as hospitals, in practice. Further, operations of these apparatuses require specialized knowledge.

In view of this, the inventions disclosed in Japanese Patent Application Publication, Tokukaihei, No. 5-38331 A, and Japanese Patent Application Publication, Tokukaihei, No. 5-38332 A propose arterial-stiffness evaluation apparatuses using a cuff. However, the techniques according to the inventions are merely such that a pulse wave is detected from cuff pressure, and how much the amplitude of the pulse wave changes in height is evaluated.

Further, the inventions disclosed in Japanese Patent Application Publication, Tokukai, No. 2004-223046 A, and Japanese Patent Application Publication, Tokukaihei, No. 7-124129 A propose arterial-stiffness evaluation apparatuses using a cuff. These inventions propose techniques that consider a relationship between (a) a difference between internal force and external force exerted on a wall of an artery and (b) a diameter of the artery. In the techniques, the relationship between (a) a transmural pressure across a vascular wall and (b) a vascular diameter is directly derived with the use of blood pressure and amplitude of a pulse wave detected by a cuff. The techniques requires to estimate beforehand a given function that defines the relationship between (a) the transmural pressure applied to a wall of a blood vessel and (b) the diameter of the blood vessel. Accordingly, an obtainable result obviously depends on the estimated function. This causes such a problem that the ground on whether a way of estimating the function is reasonable or not is poor.

CITATION LIST

Patent Literature 1
Japanese Patent Application Publication, Tokukaihei, No. 5-38331 A (Publication Date: Feb. 19, 1993)
Patent Literature 2
Japanese Patent Application Publication, Tokukaihei, No. 5-38332 A (Publication Date: Feb. 19, 1993)
Patent Literature 3
Japanese Patent Application Publication, Tokukai, No. 2004-223046 A (Publication Date: Aug. 12, 2004)

SUMMARY OF INVENTION

Those who want to evaluate blood vessel stiffness by the conventional techniques should visit facilities such as hospitals, and pay for inspection charge every time they receive checkup for measurement of the blood vessel stiffness. Further, they need to accommodate schedules of apparatuses or facilities, which naturally causes temporal restrictions. From this viewpoint, as it stands now, it cannot be said that anyone can evaluate blood vessel stiffness anytime he or she wants.

Further, in the techniques disclosed in Patent Literatures 1 and 2, the measurement is performed without considering characteristics of vascular walls. In view of this, it cannot be said that the vascular wall stiffness is evaluated accurately. Moreover, the technique disclosed in Patent Literature 3 is questioned in theory as the evaluation method for evaluating the stiffness of a vascular wall, as has been already described above. In view of this, there are serious doubts as to whether or not the vascular wall stiffness is evaluated accurately.

In view of this, the present invention aims to provide an arterial-wall stiffness evaluation system in which anybody can easily evaluate blood vessel stiffness anytime at home without any specialized knowledge, and it is possible to evaluate the blood vessel stiffness with more accuracy than the conventional similar techniques.

In order to achieve the above object, an arterial-wall stiffness evaluation system according to the present invention includes: a cuff to be attached to a part of a living body; a pressure sensor for detecting air pressure in the cuff; cuff-pressure control means for controlling the pressure in the cuff to be increased or decreased to a predetermined value, based on a value detected by the pressure sensor (in other words, cuff-pressure control means for controlling inner pressure of the cuff based on a value detected by the pressure sensor; and data processing means for calculating, based on pulse waves detected by the pressure sensor, pulse-wave amplitudes of cuff-pressure pulse waves and blood-pressure pulse waves, and for evaluating arterial-wall stiffness based on the pulse-wave amplitudes.

Further, an arterial-wall stiffness evaluation system according to the present invention has the arrangement of the aforementioned arterial-wall stiffness evaluation system, and is arranged such that the arterial-wall stiffness is evaluated by estimating a pressure-diameter characteristic curve, which represents a relationship between vascular diameter and transmural pressure applied to a vascular wall. The arterial-wall stiffness may be evaluated by estimation from shapes and amplitudes of the pulse waves detected by the pressure sensor. The arterial-wall stiffness may be evaluated by estimating, from the pulse waves thus detected, a differential function obtainable by differentiating a pressure-diameter characteristic curve with respect to transmural pressure. Further, the arterial-wall stiffness may be evaluated by estimating a pressure-diameter characteristic curve by numerically integrating the pressure-diameter characteristic curve thus differentiated. Alternatively, the arterial-wall stiffness may be evaluated by use of values of parameters determined by identifying a function that is most fit to the pressure-diameter characteristic curve thus estimated. As the function, an arctan or a sigmoid function is used. Further, with the use of such techniques, the evaluation of the arterial-wall stiffness is robust with respect to accidental movement such as body motion.

Additional objects, features, and strengths of the present invention will be made clear by the description below. Further, the advantages of the present invention will be evident from the following explanation in reference to the drawings.

DESCRIPTION OF EMBODIMENTS

As has been already described above, the present invention is aimed at achieving the aforementioned object that anyone can easily evaluate blood vessel stiffness anytime with high accuracy at home without special knowledge. The object of the present invention is attainable by including: a cuff to be attached to a part of a living body; a pressure sensor for detecting pressure in the cuff; cuff-pressure control means for controlling the pressure in the cuff to be increased or decreased to a given value, based on a value detected by the pressure sensor; and data processing means for calculating pulse-wave amplitudes of cuff-pressure pulse waves and blood-pressure pulse waves based on pulse waves detected by the pressure sensor, and for evaluating arterial-wall stiffness based on the pulse-wave amplitude thus calculated.

Embodiment 1

Figure 1:
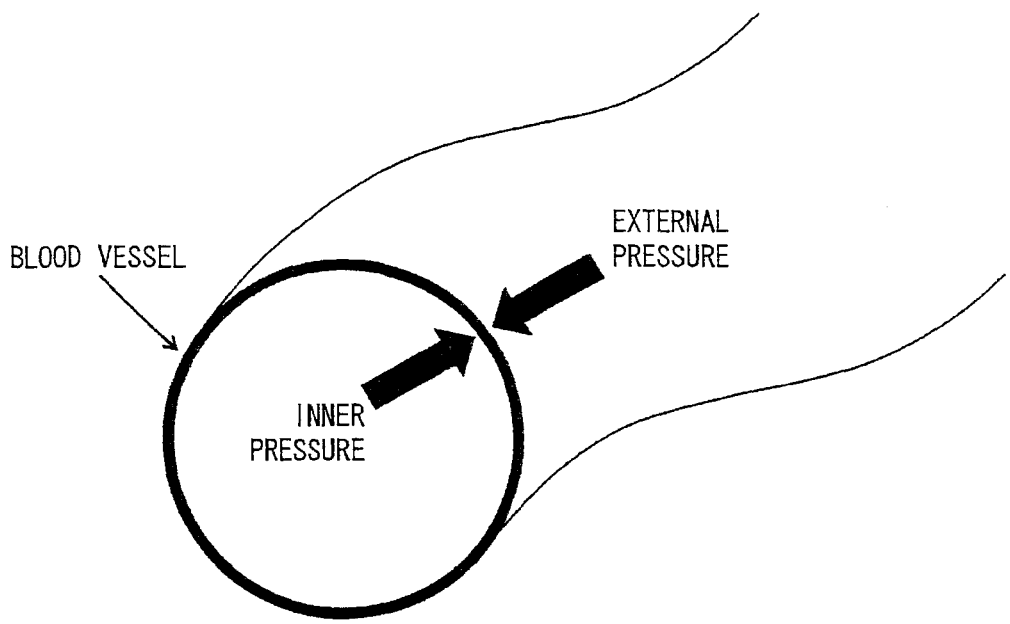
FIG. 1 is an explanatory diagram illustrating a transmural pressure of a blood vessel.

For example, as illustrated in FIG. 1, a vascular diameter of a blood vessel is determined by (i) a difference (a transmural pressure) between pressure exerted from the inside of the blood vessel toward the outside and pressure exerted on the blood vessel from the outside, and (ii) material characteristics of the blood vessel. The transmural pressure is defined such that the transmural pressure=inner pressure−external pressure. When the transmural pressure is negative, i.e., when the external pressure is higher than the inner pressure, the vascular diameter becomes small. Meanwhile, when the transmural pressure is positive, the blood vessel is dilated. Thus, when the transmural pressure is determined, the vascular diameter is determined. In view of this, the vascular diameter can be expressed as a function of the transmural pressure.

Figure 2:
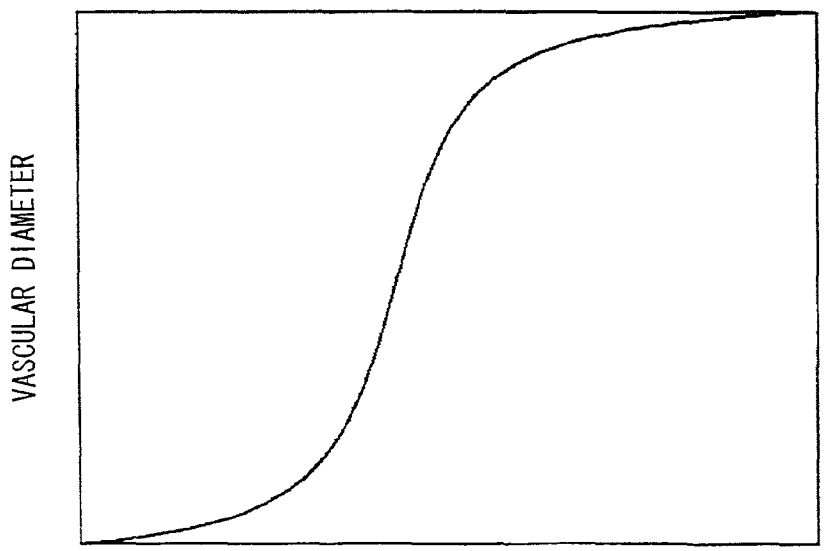
FIG. 2 is an explanatory diagram illustrating an example of a vascular pressure-diameter characteristic curve.

A maximum value that the vascular diameter would take is limited. Therefore, when the vascular diameter is depicted as the function of the transmural pressure, it exhibits a sigmoid function curve as illustrated in FIG. 2, for example. Hereinafter, the curve of the function is called "vascular pressure-diameter characteristic curve".

Figure 3:
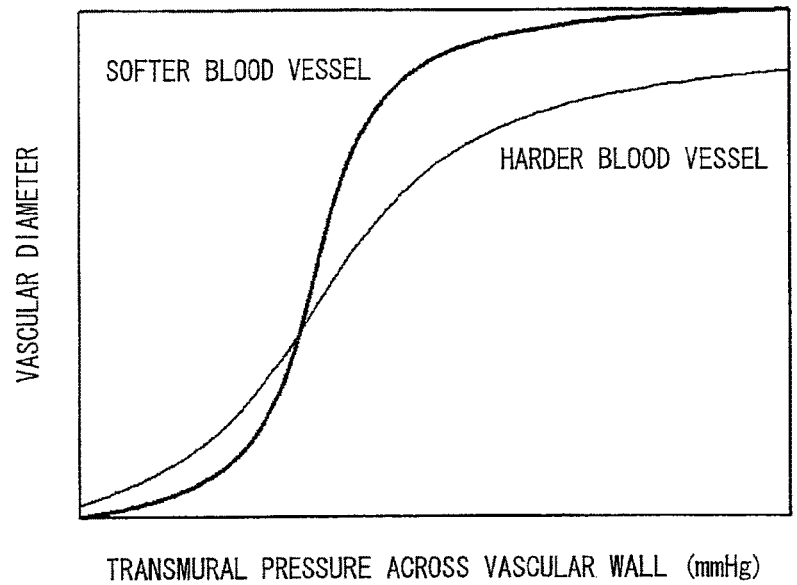
FIG. 3 illustrates an example of how the pressure-diameter characteristic curve varies depending on blood vessel stiffness.

The vascular pressure-diameter characteristic curve reflects characteristics of tissues of a vascular wall. For example, as illustrated in FIG. 3, in a case where the tissues constituting a vascular wall are hard, the characteristic curve is moderate. On the other hand, in a case where the tissues are soft, the characteristic curve is steep. The present invention takes this point into account. That is, the present invention evaluates blood vessel stiffness by estimating a vascular pressure-diameter characteristic curve. This is a feature of the present invention.

There are various possible methods for estimating the characteristic curve. For example, it is possible to appropriately estimate the characteristic curve in accordance with the following procedure. That is, the following method uses a cuff for measurement in order to estimate the characteristic curve. The measurement by a cuff has been widely used at home conventionally, and has such advantages that the measurement is simple, noninvasive, and inexpensive.

Figure 4:
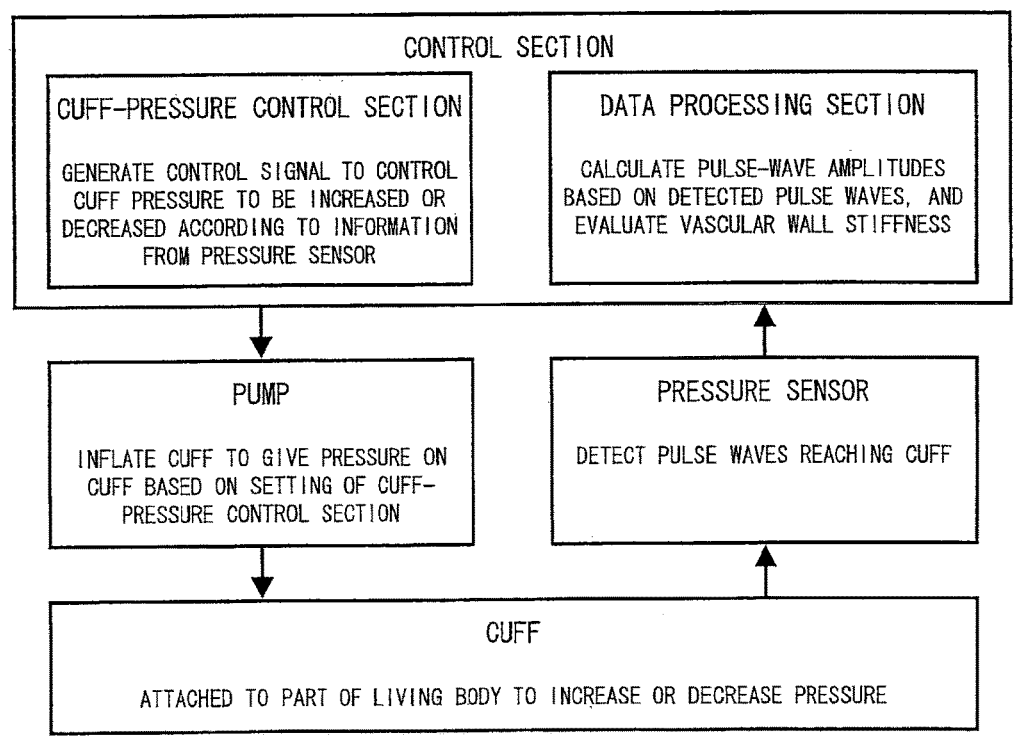
FIG. 4 illustrates an arrangement of a system of the present invention.

FIG. 4 is a functional block diagram of a simplified arterial-wall stiffness evaluation system using a cuff, according to the present invention. As illustrated in FIG. 4, a control section for controlling the whole system includes a cuff-pressure control section, thereby producing a control signal to control pressure (cuff pressure) in the cuff to be increased or decreased in accordance with information from the after-mentioned pressure sensor. Based on setting of the cuff-pressure control section, a pump for sending air to give pressure on the cuff is controlled so that the pressure of the cuff, which is attached to a part of a living body, is controlled to be increased or decreased. A pulse wave that reaches the cuff is detected by the pressure sensor. While the cuff pressure is controlled in accordance with the pressure sensor as such, the after-mentioned process is performed based on the pulse wave detected by the pressure sensor. Accordingly, calculation of amplitude of the pulse wave, evaluation on vascular wall stiffness, and the like process are performed.

When arterial-wall stiffness is evaluated actually with the use of the system, the cuff is initially attached to a part of a living body, i.e., an upper arm of the living body. After that, the pump is driven to gradually increase inner pressure of the cuff, while the inner pressure of the cuff is measured successively. At this time, sampling frequency is set to about 1000 Hz, for example. While actual pressure is detected by the pressure sensor, the cuff is inflated to increase the cuff pressure up to a value that is slightly over systolic blood pressure of a human. A target pressure is about 200 mHg.

Figure 5:
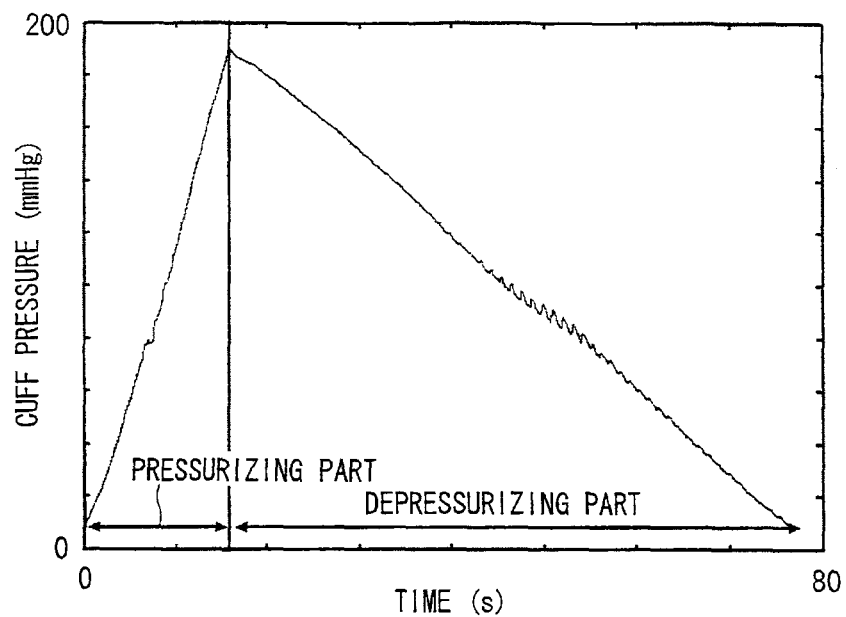
FIG. 5 illustrates an example of time-series data on how cuff pressure is changed through time.

When the cuff pressure reaches the target pressure, the air in the cuff is released to decrease the pressure at a constant speed. The depressurization rate is set so that a necessary number of beats for analysis can be recorded during the decrease in the pressure. The depressurization rate is roughly about 3 mmHg/sec, in practice. FIG. 5 illustrates time-series data of the cuff inner pressure, obtained by recording the increase and decrease in pressure described above.

Figure 6:
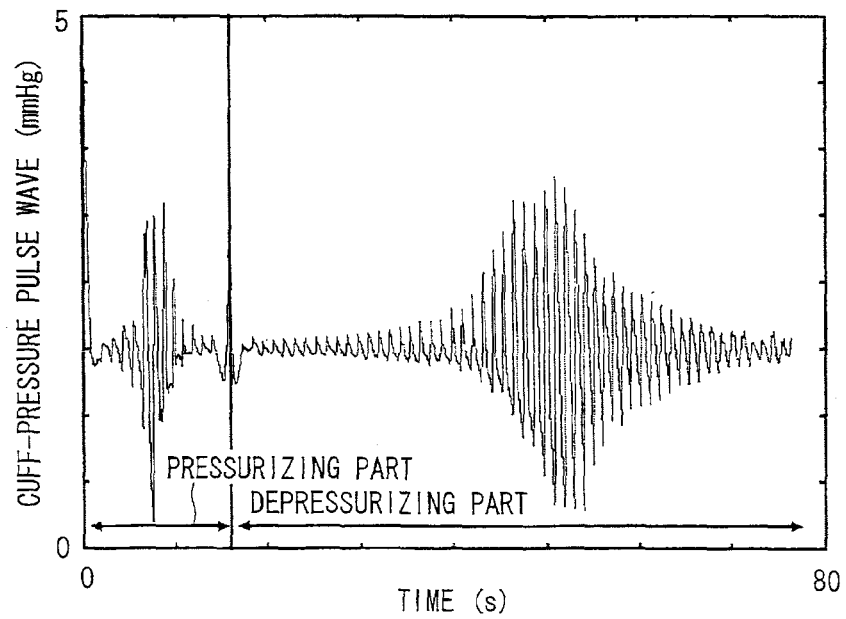
FIG. 6 illustrates a cuff-pressure pulse wave that has passed through a band-pass filter, in regard to time-series cuff pressure.
Figure 7:
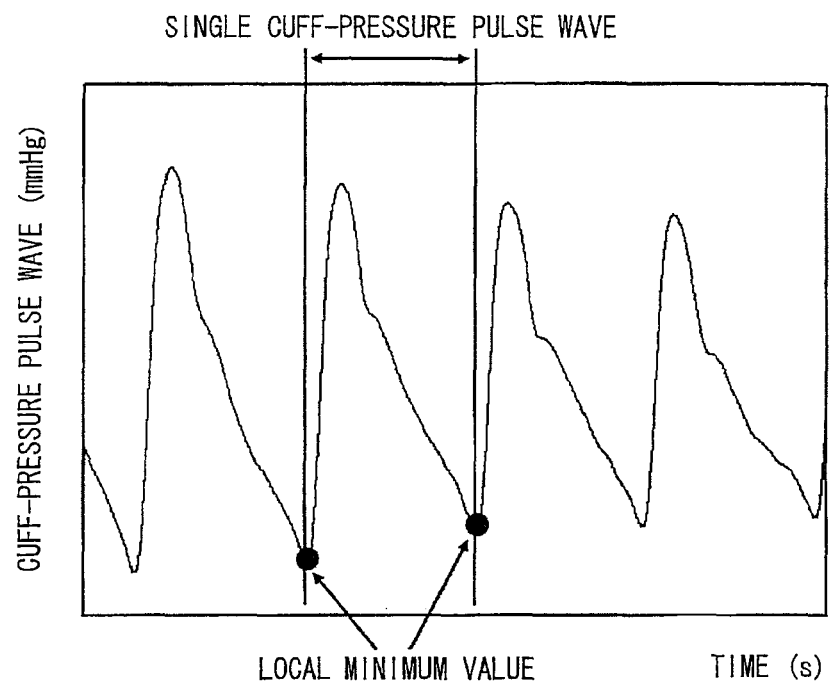
FIG. 7 illustrates a single cuff-pressure pulse wave zone in a time series of cuff-pressure pulse waves.

In the following description, the external pressure exerted on a vascular wall is assumed mainly as pressure exerted by the cuff fastening. In view of this, the transmural pressure across the vascular wall is hereinafter assumed as a difference between blood pressure and cuff pressure. To the time-series data of the cuff inner pressure thus recorded, a band-pass filter is applied so as to extract pulse-wave components, thereby obtaining cuff pulse wave data as illustrated in FIG. 6, for example. Here, a pass-frequency bandwidth is set from about 0.5 Hz to 10 Hz. Hereinafter, the cuff pulse wave data is called "time series of cuff-pressure pulse waves". Further, in a time series of cuff-pressure pulse waves as illustrated in FIG. 7, a zone from a local minimum value to a subsequent local minimum value, for example, is called a single cuff-pressure pulse wave. That is, the time series of cuff-pressure pulse waves is constituted by a plurality of cuff-pressure pulse waves continued.

Figure 8:
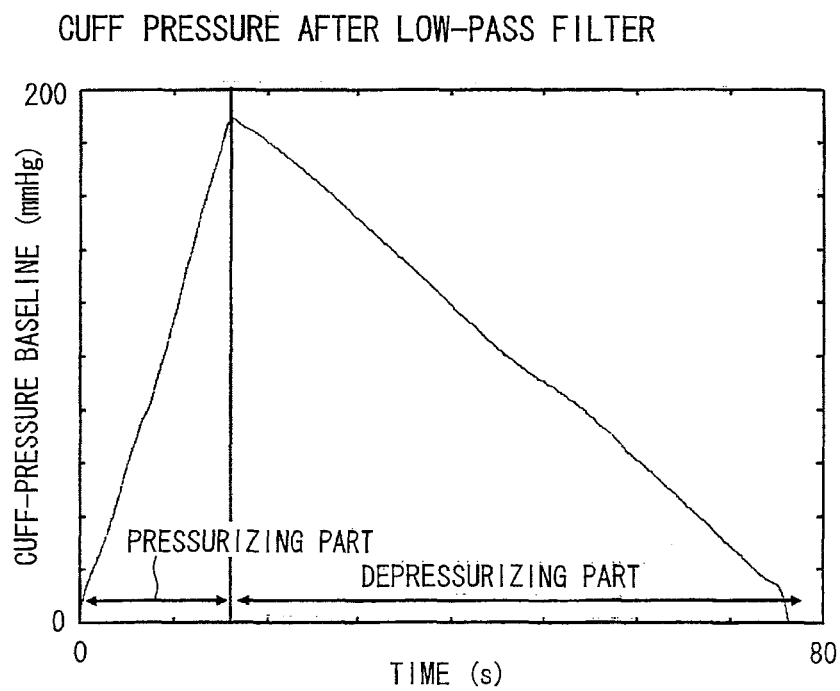
FIG. 8 illustrates cuff pressure obtained after a low-pass filter is applied to time-series data of cuff inner pressure.

Further, a low-pass filter is applied to the time-series data of the cuff inner pressure thus recorded, so as to extract a baseline of the cuff pressure, as illustrated in FIG. 8, for example. At this time, cutoff frequency is set to about 0.5 Hz. Hereinafter, the baseline of the cuff pressure is called "time series of cuff-pressure baseline". The present invention estimates a vascular pressure-diameter characteristic curve with the use of cuff-pressure pulse waves recorded during the decrease in pressure in the cuff, among the pulse wave components thus extracted.

Figure 9:
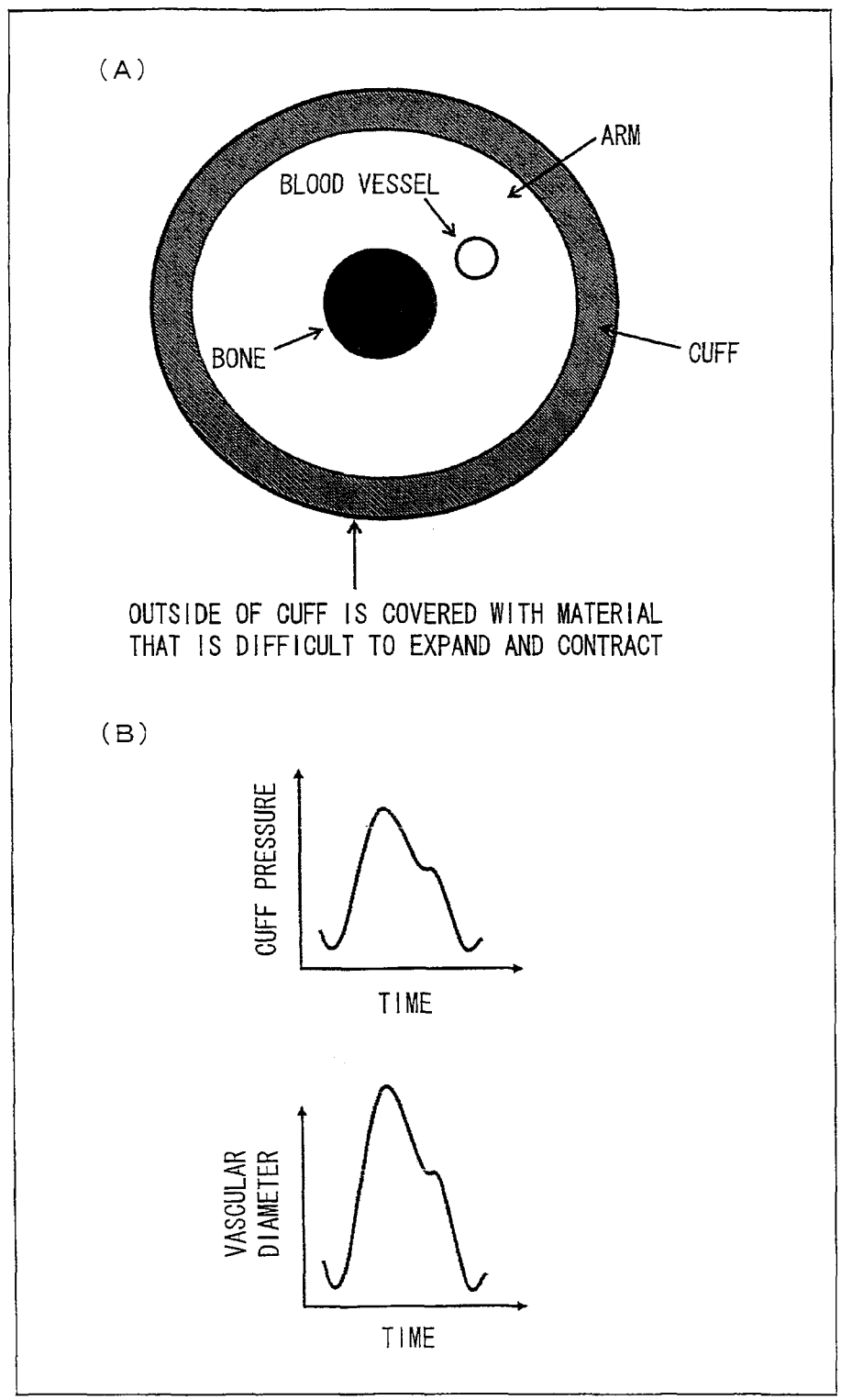
FIG. 9 illustrates how a cuff-pressure pulse wave reflects a vascular diameter. (A) and (B) of FIG. 9 each illustrate a correlation between cuff pressure and vascular diameter.

As illustrated in (A) and (B) of FIG. 9, a cuff-pressure pulse wave reflects a vascular diameter. As blood pressure increases under a constant external pressure, the transmural pressure applied to a vascular wall becomes large toward a positive direction, thereby resulting in that a vascular diameter and a vascular volume increase. The outside of the cuff is covered with a material that is difficult to expand and contract, and therefore, the increase in the vascular volume gives pressure on the cuff, with the result that the cuff inner pressure increases. In contrast, when the blood pressure decreases, the vascular diameter becomes small and the cuff pressure decreases.

Figure 10:
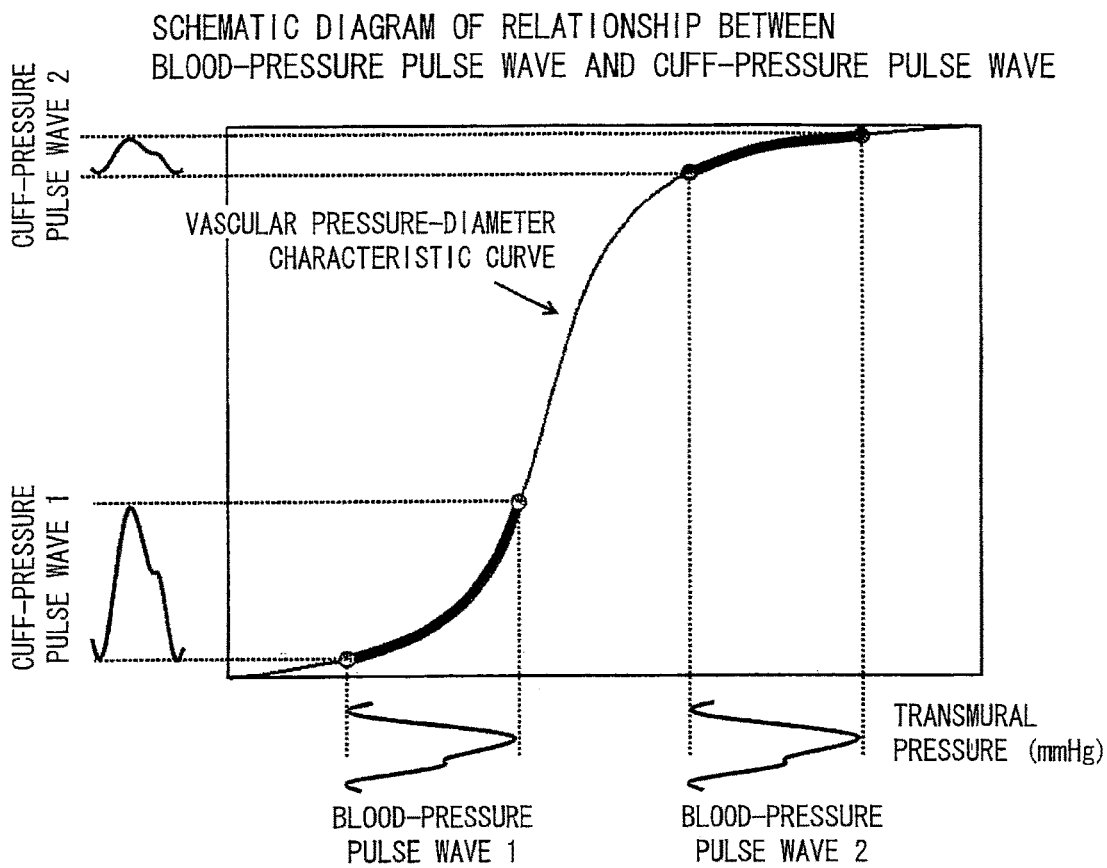
FIG. 10 is a schematic diagram illustrating a relationship between blood-pressure pulse wave and cuff-pressure pulse wave.

The size and shape of the cuff-pressure pulse wave and the transmural pressure can be associated with each other via a vascular pressure-diameter characteristic curve, as illustrated in FIG. 10. At this time, under different external pressures, pulse waves caused by the same change in blood pressure are measured as cuff-pressure pulse waves having different size. For example, in FIG. 10, a blood-pressure pulse wave 1 occurring when the external pressure is large is measured as a cuff-pressure pulse wave 1. On the other hand, a blood-pressure pulse wave 2 occurring when the external pressure is small is measured as a cuff-pressure pulse wave 2.

Here, just the blood-pressure pulse wave and the cuff-pressure pulse wave are measurable, and the transmural pressure has been already found out. However, since the vascular pressure-diameter characteristic curve has not been obtained yet, where in FIG. 10 each of the cuff-pressure pulse waves is to be positioned in a vertical direction cannot be determined. For this reason, the vascular pressure-diameter characteristic curve cannot be directly estimated from the blood-pressure pulse waves and the cuff-pressure pulse waves.

Figure 11:
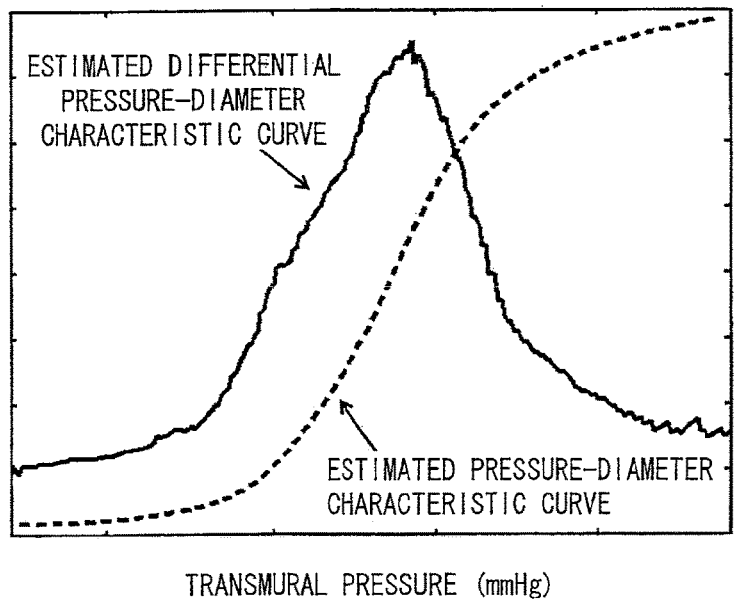
FIG. 11 illustrates how a pressure-diameter characteristic curve of a blood vessel is estimated by use of a cuff-pressure pulse wave.

In view of this, the present invention proposes the following procedure to estimate a vascular pressure-diameter characteristic curve by use of cuff-pressure pulse waves, for example (see FIG. 11). Initially, a curve obtainable by differentiating a vascular pressure-diameter characteristic curve with respect to a transmural pressure is estimated from a cuff-pressure pulse wave. Hereinafter, the curve is called differential pressure-diameter characteristic curve. Subsequently, the differential pressure-diameter characteristic curve thus estimated is numerically integrated, so as to estimate a vascular pressure-diameter characteristic curve.

Figure 12:
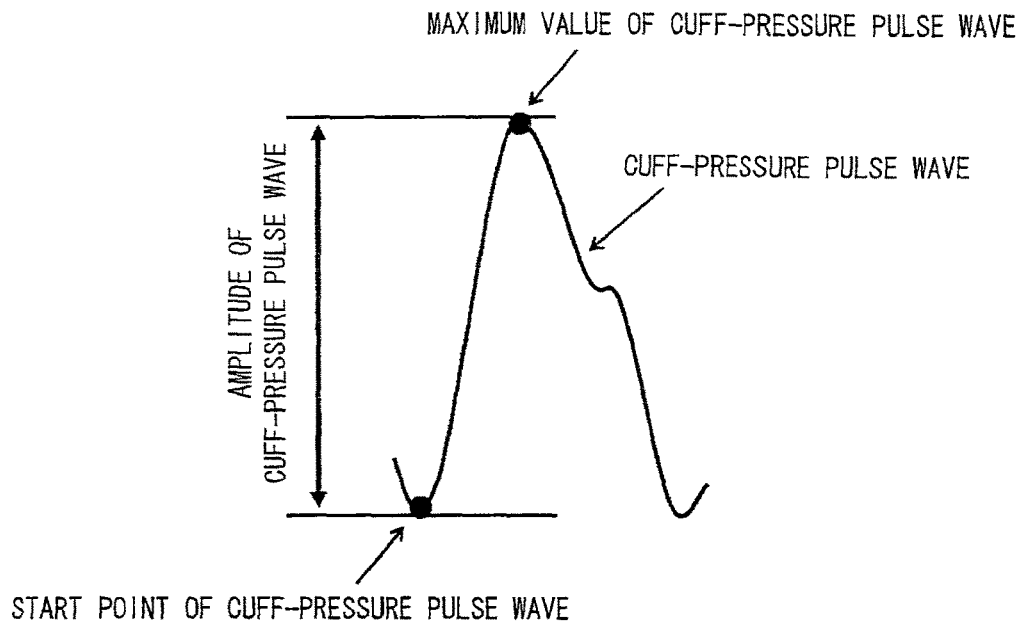
FIG. 12 illustrates amplitude of a cuff-pressure pulse wave.

There are two different methods as a method for estimating such a differential pressure-diameter characteristic curve, as follows:

Method 1:

Initially, amplitude of an extracted cuff-pressure pulse wave is found. For example, as illustrated in FIG. 12, a height from a start point (local minimum value) of a cuff-pressure pulse wave to a point of a maximum value of the cuff-pressure pulse wave is taken as the amplitude. A ratio between an amplitude of a given cuff-pressure pulse wave and a pulse pressure (=a difference between systolic blood pressure and diastolic blood pressure) is an estimated value of an average gradient in a given zone in a vascular pressure-diameter characteristic curve.

Figure 13:
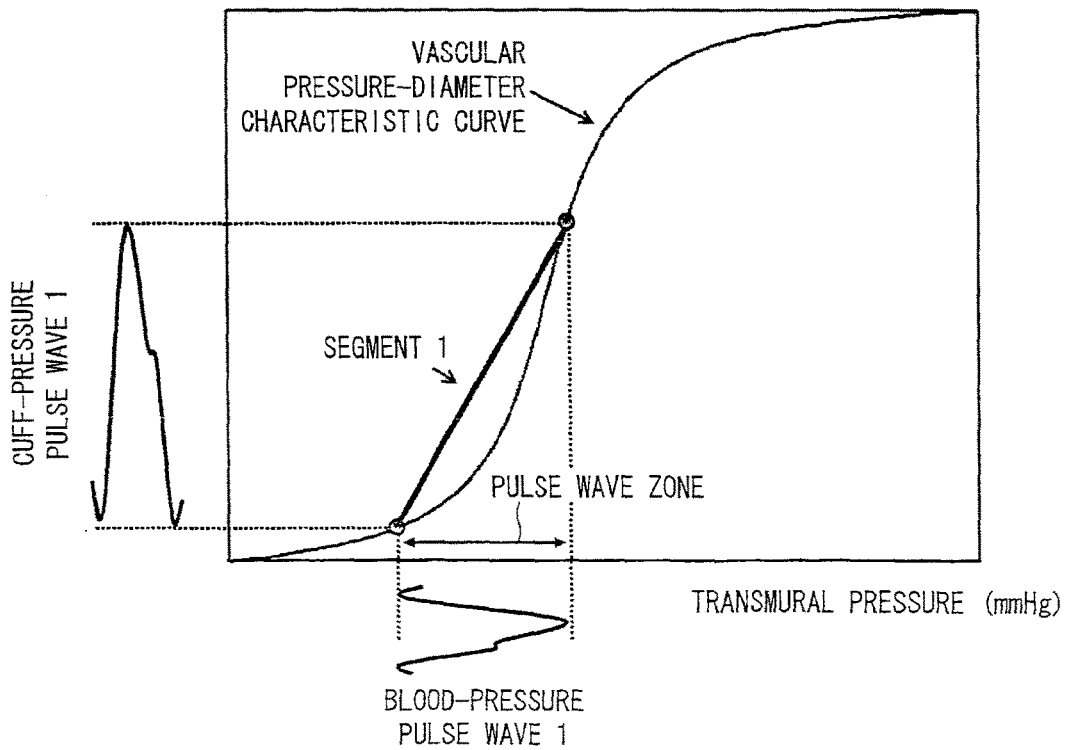
FIG. 13 illustrates that a ratio between amplitude of a cuff-pressure pulse wave and pulse pressure is an estimated value of an average gradient in a given zone of a vascular pressure-diameter characteristic curve.

FIG. 13 illustrates an example of this. A blood-pressure pulse wave 1 occurring when a given transmural pressure is applied to a blood vessel is measured as a cuff-pressure pulse wave 1 that reflects the vascular pressure-diameter characteristic curve. With the use of the amplitude of the cuff-pressure pulse wave and the pulse pressure, a segment 1 is formed on a pressure-diameter characteristic curve. A gradient of the segment 1 coincides with an average gradient of the pressure-diameter characteristic curve within a zone in which the segment 1 is formed as such. Hereinafter, the zone is called as a pulse-wave zone with respect to the pulse wave. A width of each pulse-wave zone coincides with a corresponding pulse pressure. In the same manner, respective average gradients of the pressure-diameter characteristic curve within pulse-wave zones corresponding to respective pulse waves are found.

Figure 14:
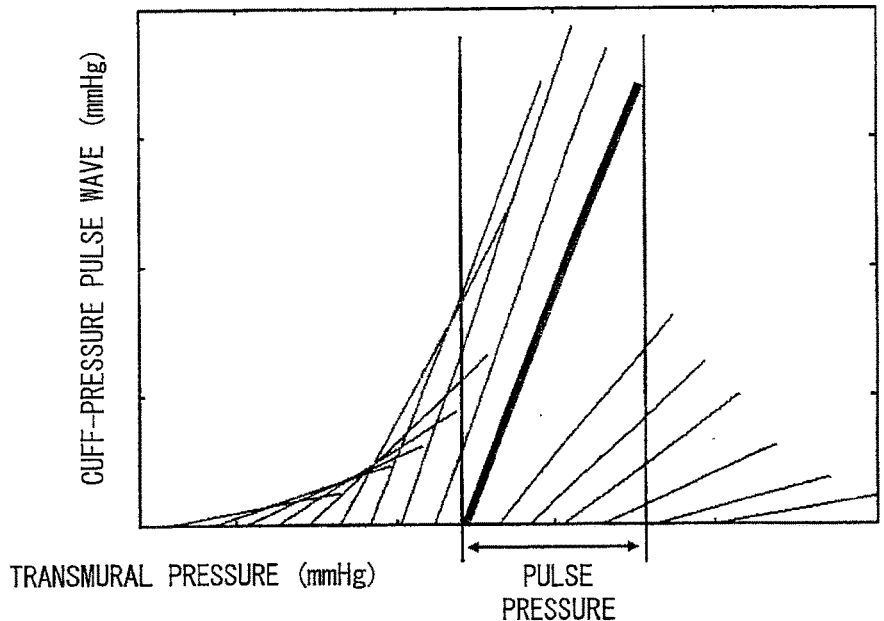
FIG. 14 illustrates how to find an average gradient of a pressure-diameter characteristic curve in a vascular channel of each pulse wave.

Segments of the respective pulse waves, formed in the same manner as the segment 1 in FIG. 13, are shown in FIG. 14. In FIG. 14, the segments are shown in such a manner that start points of the segments are aligned on an X-axis. A differential value of the pressure-diameter characteristic curve at a given transmural pressure of P mmHg is defined as an average value of average gradients in all pulse-wave zones that include the transmural pressure of P.

Figure 15:
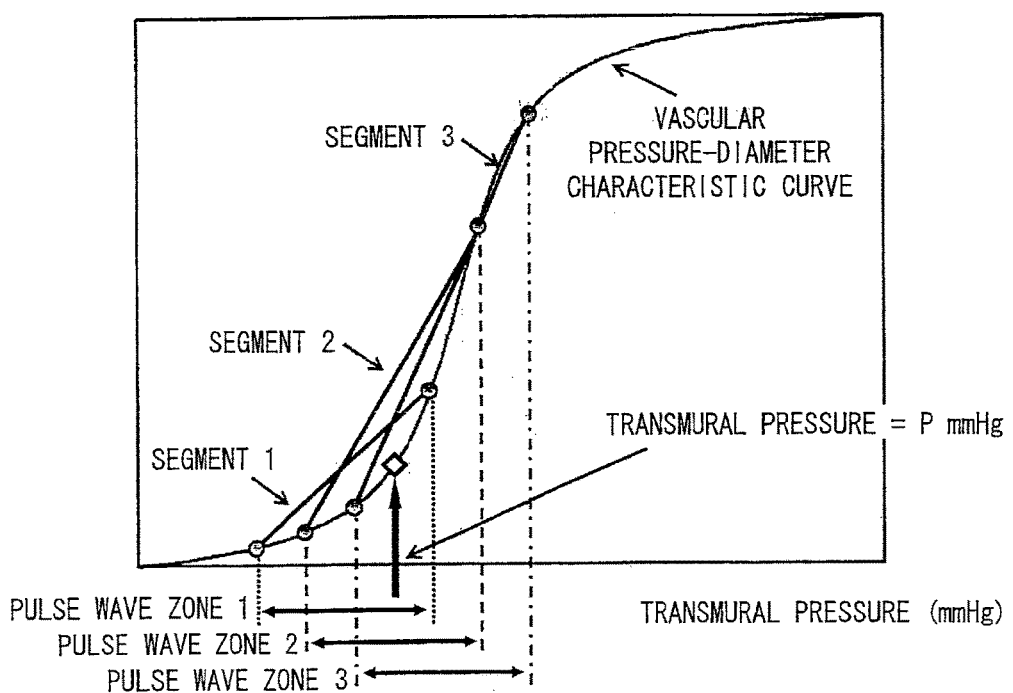
FIG. 15 illustrates that a differential value of a pressure-diameter characteristic curve at a given transmural pressure is represented as an average value of average gradients of all pulse wave zones including the given transmural pressure.

FIG. 15 illustrates a case where the differential value of the pressure-diameter characteristic curve at the transmural pressure of P mmHg is found. Here, the pulse-wave zones including the transmural pressure of P are pulse-wave zones 1, 2, and 3. The differential value of the pressure-diameter characteristic curve at the transmural pressure of P is obtained as an average value of gradients of segments 1, 2, and 3. With the use of the method, differential values of the vascular pressure-diameter characteristic curve at various values of the transmural pressure are found. From the differential values thus obtained, a differential pressure-diameter characteristic curve is estimated.

Figure 16:
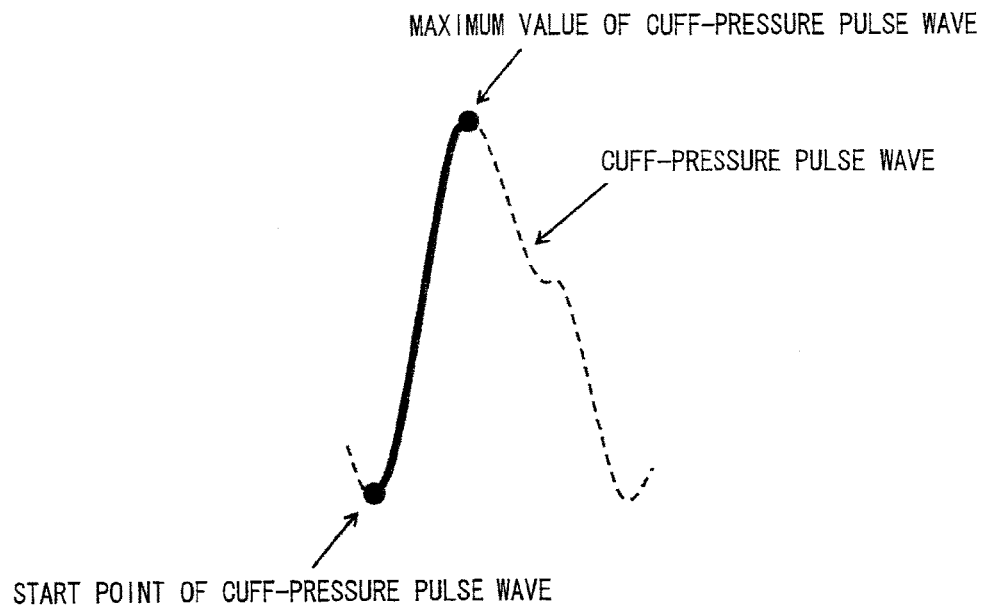
FIG. 16 illustrates a zone from a local minimum value that is a start point of an extracted cuff-pressure pulse wave, up to a maximum value.
Figure 17:
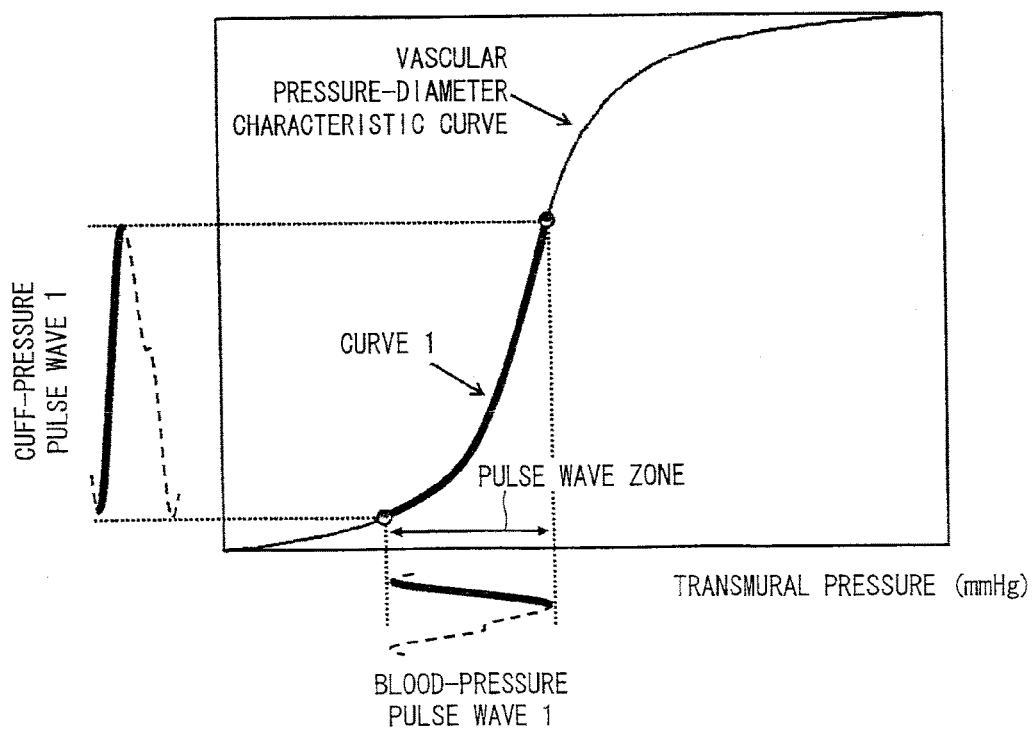
FIG. 17 illustrates how a curve 1 is made by use of a zone corresponding to a blood-pressure pulse wave and a cuff-pressure pulse wave.
Figure 18:
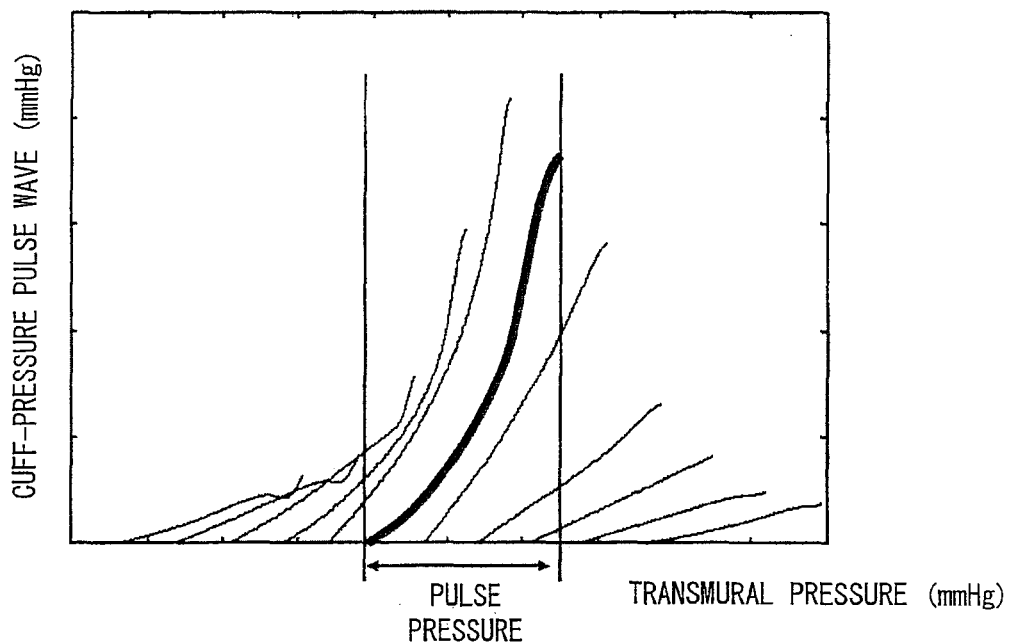
FIG. 18 is a view of an example of segments taken in the same manner as the curve 1, in which view the segments are illustrated in such a manner that start points of the curves are aligned on an X-axis.

Method 2:

As illustrated in FIG. 16, a zone from a local minimum value, which is a start point, of an extracted cuff-pressure pulse wave to a maximum value of the extracted cuff-pressure pulse wave is taken, for example. The zone corresponds to a course of a blood-pressure pulse wave from diastolic blood pressure to systolic blood pressure. As illustrated in FIG. 17, a curve 1 is formed based on a zone corresponding to a blood-pressure pulse wave 1 and a cuff-pressure pulse wave 1. The curve 1 can be assumed as an estimated part of a vascular pressure-diameter characteristic curve. FIG. 18 shows segments of respective pulse waves, formed in the same manner as the curve 1 in FIG. 17. In FIG. 18, the curves are shown in such a manner that start points of the curves are aligned on an X-axis.

Figure 19:
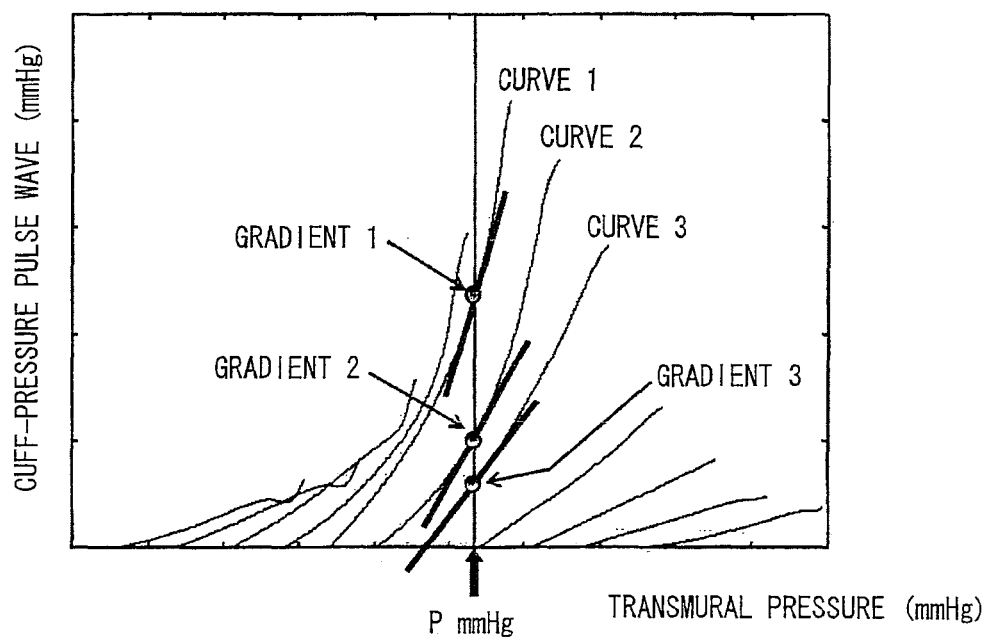
FIG. 19 illustrates a case where a differential value of a pressure-diameter characteristic curve is found when a transmural pressure is P mmHg.

A differential value of the pressure-diameter characteristic curve at a given transmural pressure of P mmHg, is obtained as follows: Initially calculated are gradients of portions near P in curves in all pulse-wave zones that include the transmural pressure of P. Subsequently, an average value of the gradients is calculated. The average value of the gradients is taken as a differential value of the pressure-diameter characteristic curve at the transmural pressure of P. FIG. 19 illustrates an example of a case where the differential value of the pressure-diameter characteristic curve at the transmural pressure of P mmHg is found.

In this example, there are three zones as the pulse-wave zone including the transmural pressure of P, and curves formed in the respective pulse-wave zones are curves 1, 2, and 3. The gradients of the curves 1, 2, and 3 at the transmural pressure of P are gradients 1, 2, and 3, respectively. The differential value of the pressure-diameter characteristic curve at the transmural pressure of P is obtained as an average value of the gradients 1, 2, and 3. In the same manner, differential values of the vascular pressure-diameter characteristic curve at other values of the transmural pressure are obtained in the same manner. From the differential values thus obtained, a differential pressure-diameter characteristic curve is estimated.

The differential pressure-diameter characteristic curve obtained as such is numerically integrated, thereby finding a pressure-diameter characteristic curve. In this way, the vascular pressure-diameter characteristic curve can be estimated.

In the present invention, in order to evaluate vascular wall stiffness from the vascular pressure-diameter characteristic curve thus estimated, a function that is most fit to the estimated vascular pressure-diameter characteristic curve is determined, and the evaluation is performed with the use of values of parameters identified by the determination of the fitted function. There are two different methods as the evaluation method, as exemplified below. Note that there are other methods in which various functions may be used, similarly.

Figure 20:
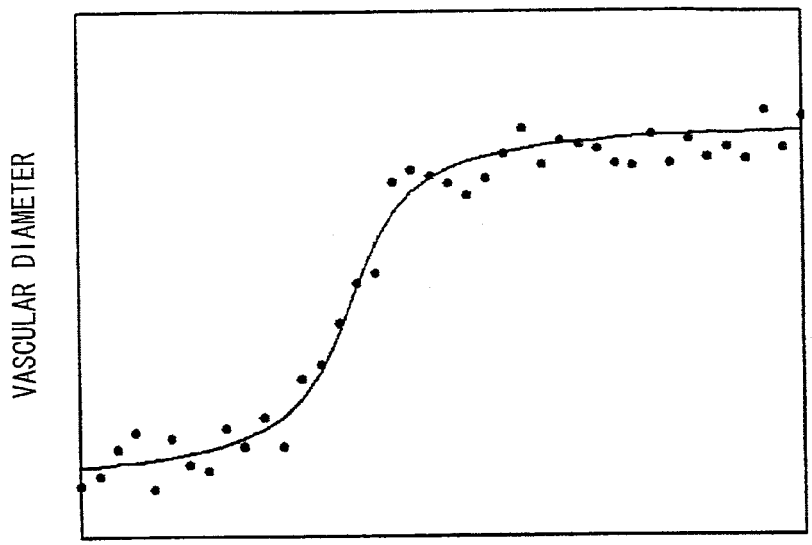
FIG. 20 illustrates an example of an arctan that is most fit to an obtained vascular pressure-diameter characteristic curve.

Method 1:

An arctan that is most fit to the estimated vascular pressure-diameter characteristic curve is found, for example, as illustrated in FIG. 20. The equation used for this is represented as follows:

$$g(x) = A \cdot \arctan(B \cdot x + C) + D \qquad \text{[Math. 1]}$$

With the use of values of parameters identified by fitting of this function, arterial stiffness is evaluated. For example, when a parameter B is small, it is evaluated that the vascular wall is hard, whereas when the parameter B is large, it is evaluated that the vascular wall is soft.

Figure 21:
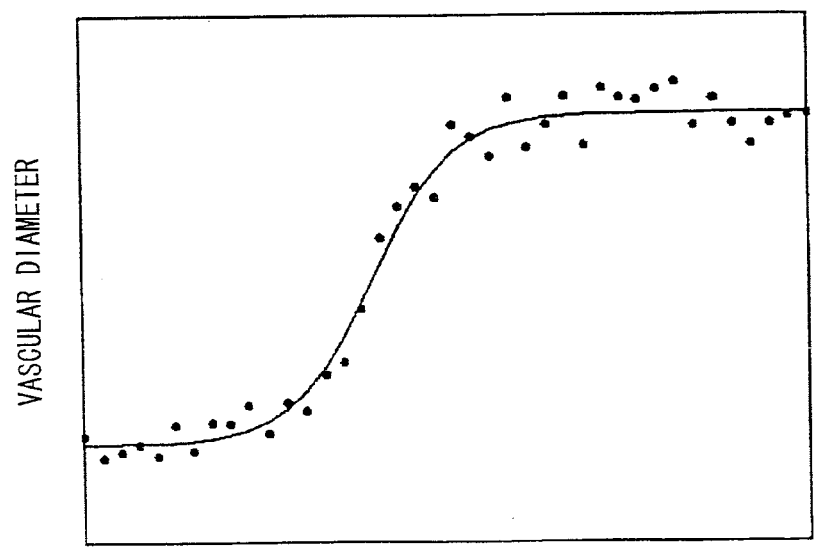
FIG. 21 illustrates an example of a sigmoid arctan that is most fit to an obtained vascular pressure-diameter characteristic curve.

Method 2:

A sigmoid function that is most fit to the estimated vascular pressure-diameter characteristic curve is found, for example, as illustrated in FIG. 21. The equation used for this is represented as follows:

$$g(x) = \frac{A}{1 + \exp(-B \cdot x + C)} + D \qquad \text{[Math. 2]}$$

With the use of values of parameters identified by fitting of this function, arterial stiffness is evaluated. For example, when a parameter B is small, it is evaluated that the vascular wall is hard, whereas when the parameter B is large, it is evaluated that the vascular wall is soft.

An arterial-wall stiffness evaluation method proposed in the present invention as above has stable system characteristics and is robust with respect to accidental movement like body motion because of the following three reasons: (i) a plurality of pieces of pulse wave information are put together to estimate a differential pressure-diameter characteristic curve; (ii) a numerical integral calculation of the differential pressure-diameter characteristic curve to estimate a pressure-diameter characteristic curve plays a role of a low-pass filter; and (iii) a calculation of function fitting to a pressure-diameter characteristic curve, which is performed to estimate vascular wall stiffness, contributes to removal of a noise element.

Figure 22:
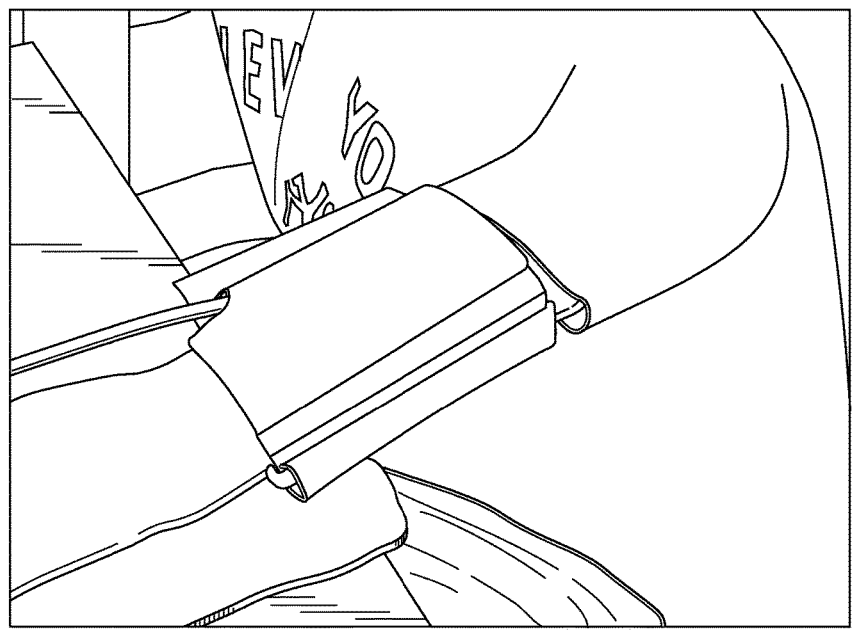
FIG. 22 illustrates how the present invention is put into use.

As described above, the present invention makes it possible to easily evaluate arterial-wall stiffness at home with the use of a cuff that has been widely used to measure blood pressure conventionally. The evaluation is performed in a manner as illustrated in FIG. 22, for example.

Further, the present invention allows anyone to easily evaluate blood vessel stiffness even at home without any specialized knowledge. Further, in the present invention, it is possible to evaluate blood vessel stiffness more accurately than conventional similar techniques.

That is, with the present invention, it is possible to easily evaluate blood vessel stiffness even at home simply by increasing and decreasing pressure of a cuff placed around an upper arm, in a similar manner to measurement of blood pressure. This allows anybody to easily evaluate stiffness of the brachial artery anywhere at any time, in order to prevent arteriosclerosis that leads to heart disease, cerebrovascular accident, and the like. Thus, the present invention can provide an important technique in view of preventive medicine.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

The invention claimed is:

1. An arterial-wall stiffness evaluation system comprising:
a cuff to be attached to a part of a living body:
a pressure sensor for detecting pressure in the cuff, and
a control section including
a cuff-pressure control section for controlling the pressure in the cuff to be increased or decreased to a predetermined value, based on a value detected by the pressure sensor; and
a data processing section for calculating, based on pulse waves detected by the pressure sensor, pulse-wave amplitudes of cuff-pressure pulse waves and blood-pressure pulse waves, and for evaluating arterial-wall stiffness based on the pulse-wave amplitudes thus calculated,
wherein said data processing section performs the following steps of:
i) obtaining respective ratios between amplitudes of extracted cuff-pressure pulse waves and corresponding pulse pressures in respective pulse-wave zones including a transmural pressure of P applied to a vascular wall and determining an average value of the respective ratios as a differential value corresponding to the transmural pressure of P applied to a vascular wall, wherein a pulse-wave zone is a zone on an axis representing the transmural pressure which zone corresponds to an amplitude of a blood-pressure pulse wave at a certain time point;

ii) performing the step i) twice or more so as to obtain a plurality of average values each being the average value obtained in the step i), and obtaining a set of points respectively corresponding to the plurality of average values;

iii) fitting a curve determined by a differentiated arctan function to the set of points;

iv) determining the arterial-wall stiffness according to a parameter of the differentiated arctan function; and v) outputting said arterial-wall stiffness to a user.

* * * * *